US011116800B2

(12) United States Patent
Tseng et al.

(10) Patent No.: US 11,116,800 B2
(45) Date of Patent: *Sep. 14, 2021

(54) COMPOSITIONS OF MORSELIZED UMBILICAL CORD AND/OR AMNIOTIC MEMBRANE AND METHODS OF USE THEREOF

(71) Applicant: TissueTech, Inc., Miami, FL (US)

(72) Inventors: Scheffer Tseng, Pinecrest, FL (US); Lorraine Chua, Miami, FL (US)

(73) Assignee: TISSUETECH, INC., Miami, FL (US)

( * ) Notice: Subject to any disclaimer, the term of this patent is extended or adjusted under 35 U.S.C. 154(b) by 229 days.

This patent is subject to a terminal disclaimer.

(21) Appl. No.: 15/727,445

(22) Filed: Oct. 6, 2017

(65) Prior Publication Data
US 2018/0064764 A1 Mar. 8, 2018

Related U.S. Application Data

(63) Continuation of application No. 14/729,489, filed on Jun. 3, 2015, now Pat. No. 90,808,491.

(60) Provisional application No. 62/109,483, filed on Jan. 29, 2015, provisional application No. 62/007,167, filed on Jun. 3, 2014.

(51) Int. Cl.
| | |
|---|---|
| *A61K 35/50* | (2015.01) |
| *A61K 35/51* | (2015.01) |
| *A61K 9/70* | (2006.01) |
| *A61K 35/28* | (2015.01) |
| *A61L 27/36* | (2006.01) |
| *A61L 27/38* | (2006.01) |
| *A61L 27/54* | (2006.01) |
| *A61L 15/40* | (2006.01) |
| *A61L 15/44* | (2006.01) |

(52) U.S. Cl.
CPC ............ *A61K 35/50* (2013.01); *A61K 9/7007* (2013.01); *A61K 35/28* (2013.01); *A61K 35/51* (2013.01); *A61L 15/40* (2013.01); *A61L 15/44* (2013.01); *A61L 27/3604* (2013.01); *A61L 27/38* (2013.01); *A61L 27/54* (2013.01)

(58) Field of Classification Search
None
See application file for complete search history.

(56) References Cited

U.S. PATENT DOCUMENTS

| | | |
|---|---|---|
| 3,598,122 A | 8/1971 | Zaffaroni |
| 3,598,123 A | 8/1971 | Zaffaroni |
| 3,710,795 A | 1/1973 | Higuchi et al. |
| 3,731,683 A | 5/1973 | Zaffaroni |
| 3,742,951 A | 7/1973 | Zaffaroni |
| 3,814,097 A | 6/1974 | Ganderton et al. |
| 3,921,636 A | 11/1975 | Zaffaroni |
| 3,972,995 A | 8/1976 | Tsuk et al. |
| 3,993,072 A | 11/1976 | Zaffaroni |
| 3,993,073 A | 11/1976 | Zaffaroni |
| 3,996,934 A | 12/1976 | Zaffaroni |
| 4,031,894 A | 6/1977 | Urquhart et al. |
| 4,060,084 A | 11/1977 | Chandrasekaran et al. |
| 4,069,307 A | 1/1978 | Higuchi et al. |
| 4,077,407 A | 3/1978 | Theeuwes et al. |
| 4,201,211 A | 5/1980 | Chandrasekaran et al. |
| 4,230,105 A | 10/1980 | Harwood |
| 4,292,299 A | 9/1981 | Suzuki et al. |
| 4,292,303 A | 9/1981 | Keith et al. |
| 4,305,502 A | 12/1981 | Gregory et al. |
| 4,327,725 A | 5/1982 | Cortese et al. |
| 4,347,841 A | 9/1982 | Benyo et al. |
| 4,476,116 A | 10/1984 | Anik |
| 4,624,848 A | 11/1986 | Lee |
| 4,798,611 A | 1/1989 | Freeman, Jr. |
| 4,871,549 A | 10/1989 | Ueda et al. |
| 4,968,509 A | 11/1990 | Radebaugh et al. |
| 5,002,071 A | 3/1991 | Harrell |
| 5,011,692 A | 4/1991 | Fujioka et al. |
| 5,017,381 A | 5/1991 | Maruyama et al. |
| 5,033,252 A | 7/1991 | Carter |
| 5,052,558 A | 10/1991 | Carter |
| 5,093,487 A | 3/1992 | Brown et al. |
| 5,116,817 A | 5/1992 | Anik |
| 5,229,135 A | 7/1993 | Philippon et al. |
| 5,260,068 A | 11/1993 | Chen |
| 5,260,069 A | 11/1993 | Chen |
| 5,323,907 A | 6/1994 | Kalvelage |
| 5,336,168 A | 8/1994 | Sibalis |

(Continued)

FOREIGN PATENT DOCUMENTS

| | | |
|---|---|---|
| CN | 1193515 A | 9/1998 |
| CN | 1203794 A | 1/1999 |

(Continued)

OTHER PUBLICATIONS

Barker et al, Placenta, 1994, vol. 15, Issue 1, pp. 47-56 (abstract only) (Year: 1994).*
U.S. Appl. No. 14/886,946 Office Action dated May 28, 2019.
U.S. Appl. No. 14/886,946 Office Action dated Sep. 7, 2018.
U.S. Appl. No. 14/996,051 Office Action dated May 28, 2019.
U.S. Appl. No. 14/996,051 Office Action dated Sep. 7, 2018.
U.S. Appl. No. 15/636,227 Office Action dated Sep. 27, 2018.
U.S. Appl. No. 15/879,042 Office Action dated Jul. 8, 2019.

(Continued)

*Primary Examiner* — Allison M Fox
(74) *Attorney, Agent, or Firm* — Wilson Sonsini Goodrich & Rosati

(57) ABSTRACT

The invention relates generally to the fields of biology and life sciences. More particularly, the invention relates to compositions and methods for modulating cellular physiology and pathological processing using a combination of compounds that can be found in morselized amniotic membrane tissue and morselized umbilical cord tissue preparations.

18 Claims, 1 Drawing Sheet

(56) References Cited

U.S. PATENT DOCUMENTS

| | | |
|---|---|---|
| 5,352,668 A | 10/1994 | Burgeson et al. |
| 5,437,287 A | 8/1995 | Phillips et al. |
| 5,456,923 A | 10/1995 | Nakamichi et al. |
| 5,461,140 A | 10/1995 | Heller et al. |
| 5,508,040 A | 4/1996 | Chen |
| 5,516,527 A | 5/1996 | Curatolo |
| 5,554,593 A | 9/1996 | Nakaya et al. |
| 5,567,441 A | 10/1996 | Chen |
| 5,622,721 A | 4/1997 | Dansereau et al. |
| 5,665,378 A | 9/1997 | Davis et al. |
| 5,686,105 A | 11/1997 | Kelm et al. |
| 5,700,410 A | 12/1997 | Nakamichi et al. |
| 5,837,280 A | 11/1998 | Kenealy et al. |
| 5,837,284 A | 11/1998 | Mehta et al. |
| 5,840,329 A | 11/1998 | Bai |
| 5,869,090 A | 2/1999 | Rosenbaum |
| 5,932,545 A | 8/1999 | Henkin et al. |
| 5,977,175 A | 11/1999 | Lin |
| 6,046,160 A | 4/2000 | Obi-Tabot |
| 6,203,755 B1 | 3/2001 | Odland |
| 6,326,019 B1 | 12/2001 | Tseng |
| 6,391,452 B1 | 5/2002 | Antonsen et al. |
| 6,465,014 B1 | 10/2002 | Moroni et al. |
| 6,521,179 B1 | 2/2003 | Girardot et al. |
| 6,573,249 B2 | 6/2003 | Lezdey et al. |
| 6,632,648 B1 | 10/2003 | Kampinga et al. |
| 6,923,983 B2 | 8/2005 | Morgan et al. |
| 6,929,801 B2 | 8/2005 | Klose et al. |
| 6,932,983 B1 | 8/2005 | Straub et al. |
| 6,946,144 B1 | 9/2005 | Jordan |
| 8,071,135 B2 | 12/2011 | Liu et al. |
| 8,105,634 B2 | 1/2012 | Liu et al. |
| 8,153,162 B2 | 4/2012 | Tseng et al. |
| 8,182,840 B2 | 5/2012 | Tseng et al. |
| 8,182,841 B2 | 5/2012 | Tseng et al. |
| 8,187,639 B2 | 5/2012 | Tseng et al. |
| 8,323,701 B2 | 12/2012 | Daniel et al. |
| 8,372,437 B2 | 2/2013 | Daniel |
| 8,372,438 B2 | 2/2013 | Daniel et al. |
| 8,420,126 B2 | 4/2013 | Tseng et al. |
| 8,440,235 B2 | 5/2013 | Tseng et al. |
| 8,455,009 B2 | 6/2013 | Tseng et al. |
| 8,460,714 B2 | 6/2013 | Tseng et al. |
| 8,840,665 B2 | 9/2014 | Young et al. |
| 8,932,805 B1 | 1/2015 | Brahm |
| 8,961,617 B2 | 2/2015 | Young |
| 8,980,630 B2 | 3/2015 | Woodbury et al. |
| 9,132,156 B1 | 9/2015 | Werber et al. |
| 9,161,954 B2 | 10/2015 | Tseng et al. |
| 9,161,955 B2 | 10/2015 | Tseng et al. |
| 9,161,956 B2 | 10/2015 | Tseng et al. |
| 9,162,011 B2 | 10/2015 | Stilwell et al. |
| 9,180,145 B2 | 11/2015 | Brown et al. |
| 9,198,939 B2 | 12/2015 | Tseng et al. |
| 9,295,753 B1 | 3/2016 | Tello |
| 9,498,327 B1 | 11/2016 | Brahm |
| 9,655,948 B1 | 5/2017 | Koob et al. |
| 9,662,355 B2 | 5/2017 | Koob et al. |
| 9,682,044 B2 | 6/2017 | Tseng et al. |
| 9,682,160 B2 | 6/2017 | Tseng et al. |
| 9,694,109 B1 | 7/2017 | Brahm |
| 9,724,370 B2 | 8/2017 | Tseng et al. |
| 9,750,771 B2 | 9/2017 | Tseng et al. |
| 9,750,772 B2 | 9/2017 | Tseng et al. |
| 9,795,639 B1 | 10/2017 | Brahm |
| 9,801,975 B2 | 10/2017 | Stilwell et al. |
| 9,801,976 B2 | 10/2017 | Stilwell et al. |
| 9,803,176 B2 | 10/2017 | Patel et al. |
| 9,808,491 B2 * | 11/2017 | Tseng ................ A61K 35/50 |
| 9,814,746 B2 | 11/2017 | Werber et al. |
| 9,821,013 B2 | 11/2017 | McFetridge et al. |
| 9,827,293 B2 | 11/2017 | Koob et al. |
| 9,913,466 B2 | 3/2018 | Chang et al. |
| 9,919,078 B1 | 3/2018 | Brahm |
| 9,920,301 B2 | 3/2018 | Taghizadeh |
| 9,944,900 B2 | 4/2018 | Gage et al. |
| 9,956,248 B2 | 5/2018 | Tom et al. |
| 10,039,793 B2 | 8/2018 | Brown et al. |
| 10,105,397 B2 | 10/2018 | Morse et al. |
| 10,105,398 B2 | 10/2018 | Morse et al. |
| 10,426,731 B2 * | 10/2019 | Tseng ................ A61K 35/50 |
| 10,555,897 B1 | 2/2020 | Brahm |
| 10,555,974 B1 | 2/2020 | Brahm |
| 10,568,914 B1 | 2/2020 | Brahm |
| 2003/0064093 A1 | 4/2003 | Jordan |
| 2003/0180181 A1 | 9/2003 | Greib et al. |
| 2004/0043026 A1 | 3/2004 | Tuan et al. |
| 2004/0048796 A1 | 3/2004 | Hariri et al. |
| 2004/0057938 A1 | 3/2004 | Ghinelli |
| 2004/0126323 A1 | 7/2004 | Shevchuk et al. |
| 2004/0126878 A1 | 7/2004 | Ramos et al. |
| 2004/0209235 A1 | 10/2004 | Goldstein et al. |
| 2005/0064391 A1 | 3/2005 | Segal et al. |
| 2006/0078993 A1 | 4/2006 | Phan et al. |
| 2006/0153928 A1 | 7/2006 | Kinoshita et al. |
| 2008/0050814 A1 | 2/2008 | Allickson |
| 2008/0131522 A1 | 6/2008 | Liu et al. |
| 2008/0286378 A1 | 11/2008 | Behrens et al. |
| 2011/0212158 A1 | 9/2011 | Tom et al. |
| 2011/0307059 A1 | 12/2011 | Young et al. |
| 2011/0311491 A1 | 12/2011 | Edinger et al. |
| 2012/0010708 A1 | 1/2012 | Young et al. |
| 2012/0010727 A1 | 1/2012 | Young et al. |
| 2012/0020933 A1 | 1/2012 | Young et al. |
| 2012/0035743 A1 | 2/2012 | Young et al. |
| 2012/0035744 A1 | 2/2012 | Young et al. |
| 2012/0141595 A1 | 6/2012 | Tseng et al. |
| 2012/0189583 A1 | 7/2012 | Liu et al. |
| 2012/0263731 A1 | 10/2012 | Fraunhofer et al. |
| 2012/0294910 A1 | 11/2012 | Daniel et al. |
| 2013/0156863 A1 | 6/2013 | Tseng et al. |
| 2013/0197665 A1 | 8/2013 | Daniel et al. |
| 2013/0209524 A1 | 8/2013 | Young |
| 2013/0211502 A1 | 8/2013 | Young |
| 2013/0211504 A1 | 8/2013 | Young |
| 2013/0211511 A1 | 8/2013 | Young |
| 2013/0236506 A1 | 9/2013 | Young |
| 2013/0238100 A1 | 9/2013 | Young |
| 2013/0289724 A1 | 10/2013 | Young |
| 2013/0344162 A1 | 12/2013 | Morse et al. |
| 2013/0344163 A1 | 12/2013 | Tseng et al. |
| 2014/0050788 A1 | 2/2014 | Daniel et al. |
| 2014/0052247 A1 | 2/2014 | Daniel et al. |
| 2014/0052274 A1 | 2/2014 | Koob et al. |
| 2014/0067058 A1 | 3/2014 | Koob et al. |
| 2014/0106447 A1 | 4/2014 | Brown et al. |
| 2014/0147511 A1 | 5/2014 | Tseng et al. |
| 2014/0255496 A1 | 9/2014 | Daniel et al. |
| 2014/0255508 A1 | 9/2014 | Morse et al. |
| 2014/0271776 A1 | 9/2014 | Vines et al. |
| 2014/0294780 A1 | 10/2014 | McFetridge et al. |
| 2014/0302162 A1 | 10/2014 | Morse et al. |
| 2014/0342014 A1 | 11/2014 | Tseng et al. |
| 2014/0348940 A1 * | 11/2014 | Murphy, V ............ A61K 35/50 424/582 |
| 2015/0017255 A1 | 1/2015 | Koob et al. |
| 2015/0086634 A1 | 3/2015 | Koob et al. |
| 2015/0216912 A1 | 8/2015 | Koob |
| 2015/0250829 A1 | 9/2015 | Daniel et al. |
| 2015/0320906 A1 | 11/2015 | Broussard et al. |
| 2015/0328264 A1 | 11/2015 | Lucey et al. |
| 2015/0335686 A1 | 11/2015 | Spencer et al. |
| 2015/0342998 A1 | 12/2015 | Tseng et al. |
| 2016/0067287 A1 | 3/2016 | McQueen et al. |
| 2016/0082152 A1 | 3/2016 | Brahm |
| 2016/0106785 A1 | 4/2016 | Tseng et al. |
| 2016/0129049 A1 | 5/2016 | Tseng et al. |
| 2016/0184368 A1 | 6/2016 | Tseng et al. |
| 2016/0303171 A1 | 10/2016 | Tseng et al. |
| 2016/0324902 A1 | 11/2016 | Tseng et al. |
| 2016/0346332 A1 | 12/2016 | Spencer et al. |
| 2017/0027993 A1 | 2/2017 | Ichim |
| 2017/0136071 A1 | 5/2017 | Danilkovitch et al. |
| 2017/0258727 A1 | 9/2017 | Tseng et al. |

(56) References Cited

U.S. PATENT DOCUMENTS

| | | |
|---|---|---|
| 2017/0260500 A1 | 9/2017 | Goodman et al. |
| 2017/0326182 A1 | 11/2017 | Tseng et al. |
| 2017/0368105 A1 | 12/2017 | Sinclair et al. |
| 2018/0008649 A1 | 1/2018 | Aberman et al. |
| 2018/0017577 A1 | 1/2018 | Franco |
| 2018/0055622 A1 | 3/2018 | Tokish et al. |
| 2018/0059109 A1 | 3/2018 | Hsuan et al. |
| 2018/0064764 A1 | 3/2018 | Tseng et al. |
| 2018/0110900 A1 | 4/2018 | Korenfeld |
| 2018/0112184 A1 | 4/2018 | Kim et al. |
| 2018/0117121 A1 | 5/2018 | Koob et al. |
| 2018/0119093 A1 | 5/2018 | Kukharchuk et al. |
| 2018/0193387 A1 | 7/2018 | Tseng et al. |
| 2018/0221418 A1 | 8/2018 | Daniel et al. |
| 2019/0046585 A1 | 2/2019 | Morse et al. |
| 2019/0374584 A1 | 12/2019 | Morse et al. |

FOREIGN PATENT DOCUMENTS

| | | | |
|---|---|---|---|
| CN | 1871019 A | 11/2006 | |
| CN | 1903073 A | 1/2007 | |
| EP | 1604695 A1 | 12/2005 | |
| JP | 74043153 B | 11/1974 | |
| JP | H01256967 A | 10/1989 | |
| KR | 20010098716 A | 11/2001 | |
| WO | WO-03077794 A2 | 9/2003 | |
| WO | WO-03097809 A2 | 11/2003 | |
| WO | WO-2004026244 A2 | 4/2004 | |
| WO | WO-2004060388 A1 | 7/2004 | |
| WO | WO-2006094247 A2 | 9/2006 | |
| WO | WO-2007038686 A2 | 4/2007 | |
| WO | WO-2007071048 A1 | 6/2007 | |
| WO | WO-2011031489 A2 | 3/2011 | |
| WO | WO-2012003377 A2 | 1/2012 | |
| WO | WO 2012/112410 * | 8/2012 | ............. A61K 35/50 |
| WO | WO-2012170905 A1 | 12/2012 | |
| WO | WO-2013032938 A1 | 3/2013 | |

OTHER PUBLICATIONS

U.S. Appl. No. 13/802,204 Office Action dated Jun. 15, 2018.

U.S. Appl. No. 14/886,946 Office Action dated Jan. 8, 2018.

U.S. Appl. No. 14/996,051 Office Action dated Apr. 2, 2018.

U.S. Appl. No. 15/195,189 Office Action dated May 30, 2018.

U.S. Appl. No. 15/215,228 Office Action dated May 30, 2018.

Ahmed et al. Expression and localization of alphavbeta6 integrin in extraplacental fetal membranes: possible role in human parturition. Mol Hum Reprod 10(3):173-179 (2004).

Allred et al. A novel ELISA for measuring CD36 protein in human adipose tissue. J Lipid Res 2(2):408-415 (2011).

Ansel et al. Pharmaceutical Dosage Forms and Drug Delivery Systems. 7th ed. Philadelphia, PA: Lippincott Williams & Wilkins (1999).

Bae et al. Characterization of the Promoter Region of the Human Transforming Growth Factor-ß Type II Receptor Gene. J. Biol. Chem. 270(49):29460-29468 (1995).

Bhutto et al. Localization of Collagen XVIII and the Endostatin Portion of Collagen XVIII in Ages Human Control Eyes and Eyes with Age-Related Macular Degeneration. Invest. Ophthalmol. Vis. Sci. 45(5):1544-1552 (2004).

Border et al. Transforming Growth Factor-ß in Disease: The Dark Side of Tissue Repair. J. Clin. Invest. 90:1-7 (1992).

Chen et al. Functions of hyaluronan in wound repair. Wound Rep Reg 7:79-89 (1999).

Chen et al. Recombinant Adenovirus Coexpressing Covalent Peptide/MHC Class II Complex and B7-1: In Vitro and In Vivo Activation of Myelin Basic Protein-Specific T Cells. J. Immunol. 167:1297-1305 (2001).

Co-pending U.S. Appl. No. 15/636,227, filed Jun. 28, 2017.

Derynk et al. TGF-ß receptor signaling, Biochem. Biophys. Acta. 1333:F105-F150 (1997).

Diaz-Prado et al. Potential use of the human amniotic membrane as a scaffold in human articular cartilage repair. Cell Tissue Bank 11:183-195 (2010).

English Translation of JP74043153B (App. S45-107284) (9 pgs.) (Pub. Nov. 19, 1974).

Ericsson et al. Chapter 17: Protein extraction from solid tissue. Methods Mol Biol. 675:307-312 (2011).

Fortunato et al. Interleukin-10 and transforming growth factor-ß inhibit amniochorion tumor necrosis factor-α production by contrasting mechanisms of action: Therapeutic implications in prematurity. Am. J. Obstet. Gynecol. 177(4):803-809 (1997).

Fortunato et al. Interleukin-10 inhibition of interleukin-6 in human amniochorionic membrane: Transcriptional regulation. Am. J. Obstet. Gynecol. 175:1057-1065 (1996).

Fortunato et al. The effect of transforming growth factor and interleukin-10 on interleukin-8 release by human amniochorion may regulate histologic chorioamnionitis. Am. J. Obstet. Gynecol. 179(3):794-799 (1998).

Fries et al. Inter-alpha-inhibitor, hyaluronan and inflammation. Acta Biochim Polonica 50(3):735-742 (2003).

Gabbiani. The myofibroblast in wound healing and fibrocontractive diseases. J. Pathol. 200:500-503 (2003).

Gajiwala et al. Evaluation of lyophilised, gamma-irradiated amnion as a biological dressing. Cell Tissue Bank 5(2):73-80 (2004).

Gennaro A., ed. Remington: The Science and Practice of Pharmacy. 19th ed. Easton, PA: Mack Publishing; 1995.

Gennaro. Remington: The Science and Practice of Pharmacy. 17th ed. Easton, PA: Mack Publishing 1975.

Grande. Role of Transforming Growth Factor-ß in Tissue Injury and Repair. Proc. Soc. Exp. Biol. Med. 214:27-40 (1997).

Guo. Carbopol® Polymers for Pharmaceutical Drug Delivery Applications. Drug Delivery Technology 3(6):1-4 (2003).

Hales et al. TGF-ß-1 induces lens cells to accumulate α-smooth muscle actin, a marker for subcapsular cataracts. Curr. Eye Res. 13:885-890 (1994).

Hall et al. Liquid Extraction Surface Analysis Mass Spectrometry Method for Identifying the Presence and Severity of Nonalcoholic Fatty Liver Disease. Anal. Chem. 89(9):5161-5170 (2017).

Hanada et al. Regulation of cytokine signaling and inflammation. Cytokine & Growth Factor Reviews 13(4-5):413-421 (2002).

Hao et al. Identification of Antiangiogenic and Antiinflammatory Proteins in Human Amniotic Membrane. Cornea 19(3):348-352 (2000).

Hatano et al. Transplantation of amniotic membrane and limbal autograft in the treatment of recurrent pterygium. Clinical Ophthalmology 50(6):1101-1104 (1996) (English Abstract).

He et al. A simplified system for generating recombinant adenoviruses. PNAS USA 95:2509-2514 (1998).

He et al. Inhibition of Proliferation and Epithelial Mesenchymal Transition via Wnt and TGF-ß Signaling Pathway in an in vitro Cell Culture Based-PVR Model by HC-HA/PTX3 Purified from Amniotic Membrane. The Association for Research in Vision and Ophthalmology (ARVO) 2016 on May 1-May 5 (Washington State Convention Center, Seattle, Washington) Abstract No. 5384-B005 (2 pgs).

He et al. Suppression of activation and induction of apoptosis in RAW264.7 cells by amniotic membrane extract. Invest Ophthalmol. Vis. Sci. 49:4468-4475 (2008).

Heiligenhaus et al. Improvement of HSV-1 Necrotizing Keratitis with Amniotic Membrane Transplantation Invest Ophthalmol Vis Sci 42(9):1969-1974 (2001).

Hilmy et al. Physical and chemical properties of freeze-dried amnio-chorion membranes sterilized by y irradiation. Atom Indonesia 13(2):1-3 (1987) Abstract only.

Hori. Amniotic Membrane Transplantation and Immune Reaction. Folia Ophthalmologica Japonica 56(9):722-727 (2005) (English Abstract).

Howes et al. Receptor for Advanced Glycation End Products and Age-Related Macular Degeneration. Invest. Ophthalmol. Vis. Sci. 45(10):3713-3720 (2004).

Jester et al. Corneal Stromal Wound Healing in Refractive Surgery: the Role of Myofibroblasts. Prog. Retin. Eye Res. 18(3):311-356 (1999).

(56) References Cited

OTHER PUBLICATIONS

Jester et al. Induction of α-Smooth Muscle Actin Expression and Myofibroblast Transformation in Cultured Cornea Keratocytes. Cornea 15(5):505-516 (1996).
Keelan et al. Activin A Exerts both Pro- and -Anti-inflammatory Effects on Human Term Gestational Tissues. Placenta 21:38-43 (2000).
Kopp et al. Abrogation of Transforming Growth Factor-beta Signaling by SMAD7 Inhibits Collagen Gel Contraction of Human Dermal Fibroblasts. J. Biol. Chem. 280(22):21570-21576 (2005).
Kuriyan et al. A potential novel therapy for PVR: HC-HA/PTX3, an active matrix component of amniotic membrane, inhibits proliferation of rabbit RPE cells and is non-toxic intravitreally. The Association for Research in Vision and Ophthalmology (ARVO) 2015 meeting on May 3-May 7 (Colorado Convention Center Denver, CO) Abstract No. 1126-B028 (2 pgs).
Kuriyan et al. HC-HA/PTX3, an active matrix component of amniotic membrane, inhibits proliferation and epithelial mesenchymal transition of RPE cells: a potential novel therapy for PVR. The Association for Research in Vision and Ophthalmology (ARVO) 2015 meeting on May 3-May 7 (Colorado Convention Center Denver, CO) Abstract No. 2287-B0192 (2 pgs).
Kuznetsova et al. The N-terminal module of thrombospondin-1 interacts with the link domain of TSG-6 and enhances its covalent association with the heavy chains of inter-alpha-trypsin inhibitor. J Biol Chem 280:30899-30908 (2005).
Lawrence. Transforming Growth Factor-ß: a general review. Eur. Cytokine Netw. 7:363-374 (1996).
Lee et al. Amniotic Membrane Transplantation for Persistent Epithelial Defects with Ulceration. Am. J. Ophthalmol. 123:303-312 (1997).
Lee et al. An Agarose Gel Electrophoretic Method for Analysis of Hyaluronan Molecular Weight Distribution. Anal. Biochem. 219:278-287 (1994).
Li et al. An Experimental Study of the Effects of Human Amniotic Membrane on Human Retinal Pigment Epithelial Cell Proliferation in vitro. Acta Acadamiae Medicinae Militaris Tertia 25(5):407-409 (2003) (English Abstract).
Li et al. Reversal of myofibroblasts by amniotic membrane stromal extract. J Cell Physiol. 215(3):657-664 (2008).
Lieberman et al. Pharmaceutical Dosage Forms. Marcel Decker, New York, N. Y. (1980).
Lieberman et al. Pharmaceutical Dosage Forms. 2 Ed. 1:209-214 (1990).
Logan et al. Decorin Attenuates Gliotic Scar Formation in the Rat Cerebral Hemisphere. Exp. Neurol. 159:504-510 (1999).
Marek et al. TGF-ß- (transforming growth factor-ß) in chronic inflammatory conditions—a new diagnostic and prognostic marker? Med. Sci. Monitl. 8(7):RA145-RA151 (2002).
Massague et al. Controlling TGF-ßsignaling. Genes and Development 14:627-644 (2000).
Moller-Pedersen et al. Neutralizing antibody to TGF-ß modulates stromal fibrosis but not regression of photoablative effect following PRK. Curr. Eye Res. 17:736-747 (1998).
Monteleone et al. SMAD7 in TGF-ß-mediated negative regulation of gut inflammation. Trends in Immunology 25(10):513-517 (2004).
Na et al. Analysis of Human Amniotic Membrane Components as Proteinase Inhibitors for Development of Therapeutic Agent for Recalcitrant Keratitis. Trophoblast Res. 13:453-466 (1999).
Nakao et al. SMAD7: a new key player in TGF-b-associated disease. Trends in Molecular Medicine 8(8):361-363 (2002).
Neumann et al. High molecular weight hyaluronic acid inhibits advanced glycation endproduct-induced NF-kB activation and cytokine expression. FEBS Ltrs. 453:283-287(1999).
Nguyen et al. Sterilization of allograft bone: effects of gamma irradiations on allograft biology and biomechanics. Cell Tissue Banking 8:93-105 (2007).
Ochsner et al. Decreased expression of tumor necrosis factor-alpha-stimulated gene 6 in cumulus cells of the cyclooxygenase2 and EP2 null mice. Endocrinology 144:1008-1019 (2003).
Oikawa et al. Inhibition of Angiogenesis by 15-Deoxyspergualin. J. Antibiotics 44(9):1033-1035 (1991).
PCT/US2006/37906 International Preliminary Report on Patentability dated Apr. 1, 2008.
PCT/US2006/37906 International Search Report and Written Opinion dated Jul. 11, 2007.
PCT/US2010/46675 International Preliminary Report on Patentability dated Feb. 28, 2012.
PCT/US2010/46675 International Search Report and Written Opinion dated May 30, 2011.
PCT/US2011/042679 International Preliminary Report on Patentability dated Jan. 8, 2013.
PCT/US2011/042679 International Search Report and Written Opinion dated Mar. 9, 2012.
PCT/US2012/041685 International Preliminary Report on Patentability dated Dec. 10, 2013.
PCT/US2012/041685 International Search Report and Written Opinion dated Aug. 14, 2012.
PCT/US2012/052358 International Preliminary Report on Patentability dated Mar. 4, 2014.
PCT/US2012/052358 International Search Report and Written Opinion dated Jan. 31, 2013.
PCT/US2015/033955 International Preliminary Report on Patentability dated Dec. 15, 2016.
PCT/US2015/033955 International Search Report and Written Opinion dated Aug. 19, 2015.
Petraglia et al. Inhibin and Activin in Human Fetal Membranes: Evidence of a Local Effect on Prostaglandin Release. J. Clin. Endocrinol. Metab. 77(2):542-548 (1993).
Prabhasawat et al. Comparison of Conjunctival Autografts, Amniotic Membrane Grafts, and Primary Closure for Pterygium Excision. Ophthalmology 104:974-985 (1997).
Relucenti et al. Cumulus oophorus extracellular matrix in the human oocyte: a role for adhesive proteins. Ital J Anat Embryol 110(2 Supp 1):219-224 (2005).
Riau et al. Preservation, sterilization and de-epithelialization of human amniotic membrane for use in ocular surface reconstruction. Biomaterials 31:216-225 (2010).
Riley et al. Production of inhibin forms by the fetal membranes, decidua, placenta and fetus at parturition. Hum. Reprod. 15:578-583 (2000).
Romero et al. The natural interleukin-1 receptor antagonist in the fetal, maternal, and amniotic fluid compartments: The effect of gestational age, fetal gender, and intrauterine infection. Am. J. Obstet. Gynecol. 171:912-921 (1994).
Ronnov-Jessen et al. Induction of α-Smooth Muscle Actin by Transforming Growth Factor-ß1 in Quiescent Human Breast Gland Fibroblasts. Lab. Invest. 68:696-707 (1993).
Saltzman. Drug Administration and Drug Effectiveness. Chapter 2. Drug Delivery-Engineering Principles for Drug Therapy. Oxford Press. p. 9-19 (2001).
Salustri et al. PTX3 plays a key role in the organization of the cumulus oophorus extracellular matrix and in in vivo fertilization. Development 131:1577-1586 (2004).
Serini et al. The Fibronectin Domain ED-A Is Crucial for Myofibroblastic Phenotype Induction by Transforming Growth Factor-ß1. J. Cell. Biol. 142:873-881 (1998).
Shah et al. Control of scarring in adult wounds by neutralising antibody to transforming growth factor ß. Lancet 339:213-214 (1992).
Shortt et al. The effect of amniotic membrane preparation method on its ability to serve as a substrate for the ex-vivo expansion of limbal epithelial cells. Biomaterials 30:1056-1065 (2009).
Singh et al. Dried gamma-irradiation amniotic membrane as dressing in burn wound care. Journal of Tissue Viability 20:49-54 (2011).
Singh et al. Encyclopedia of Pharmaceutical Technology 2nd Ed. pp. 751-753 (2002).
Singh et al. Microbiological safety and clinical efficacy of radiation sterilized amniotic membranes for treatment of second-degree burns. Burns 33:505-510 (2007).
Solomon et al. Suppression of Interleukin 1a and interleukin 1b in human limbal epithelial cells cultured on the amniotic membrane stromal matrix. Br. J. Ophthalmol 85:444-449 (2001).

(56) References Cited

OTHER PUBLICATIONS

Sur et al. Anti-inflammatory and anti-platelet aggregation activity of human placental extract. Acta Pharmacol Sin 24(2):187-192 (2003).
Tan et al. Structural and Biological Comparison of Cryopreserved and Fresh Amniotic membrane Tissues. Journal Biomaterial and Tissue Engineering 4:379-388 (2014).
Temma et al. Effects of 4-hydroxy-2-nonenal, a marker of oxidative stress, on the cyclooxygenase-2 of human placenta in chorioamnionitis. Mol Hum Reprod 10(3):167-171 (2004).
Travis et al. Hyaluronan Enhances Contraction of Collagen by Smooth Muscle Cells and Adventitial Fibroblasts Role of CD44 and Implications for Constrictive Remodeling. Cir. Res. 88:77-83 (2001).
Tseng et al. Amniotic Membrane Transplantation with or without Limbal Transplantation for Corneal Surface Reconstruction in Patients with Limbal Stem Cell Deficiency. Arch Ophthalmol. 116:431-441(Apr. 1998).
Tseng et al. How Does Amniotic Membrane Work? Ocular Surface J. 2(3):177-187 (2004).
Tseng et al. Suppression of Transforming Growth Factor-Beta Isoforms, TGF-ß Receptor Type II, and Myofibroblast Differentiation in Cultured Human Corneal and Limbal Fibroblasts by Amniotic Membrane Matrix. J. Cell Physiol. 179:325-335 (1999).
U.S. Appl. No. 11/528,902 Office Action dated Apr. 2, 2009.
U.S. Appl. No. 11/528,902 Office Action dated Dec. 16, 2009.
U.S. Appl. No. 11/528,902 Office Action dated Jan. 27, 2011.
U.S. Appl. No. 11/528,902 Office Action dated Sep. 8, 2010.
U.S. Appl. No. 11/528,980 Office Action dated Aug. 11, 2009.
U.S. Appl. No. 11/528,980 Office Action dated Jan. 10, 2011.
U.S. Appl. No. 11/528,980 Office Action dated Nov. 13, 2008.
U.S. Appl. No. 11/528,980 Office Action dated Oct. 15, 2010.
U.S. Appl. No. 11/529,658 Office Action dated Apr. 3, 2009.
U.S. Appl. No. 11/529,658 Office Action dated Dec. 16, 2009.
U.S. Appl. No. 11/529,658 Office Action dated Jan. 27, 2011.
U.S. Appl. No. 11/529,658 Office Action dated Sep. 3, 2010.
U.S. Appl. No. 11/535,924 Office Action dated Dec. 16, 2009.
U.S. Appl. No. 11/535,924 Office Action dated Jan. 31, 2011.
U.S. Appl. No. 11/535,924 Office Action dated Mar. 31, 2009.
U.S. Appl. No. 11/535,924 Office Action dated Sep. 8, 2010.
U.S. Appl. No. 13/322,896 Office Action dated Jan. 20, 2016.
U.S. Appl. No. 13/322,896 Office Action dated Jul. 6, 2015.
U.S. Appl. No. 13/322,896 Office Action dated Oct. 22, 2014.
U.S. Appl. No. 13/322,896 Office Action dated Oct. 4, 2016.
U.S. Appl. No. 13/322,896 Office Action dated Sep. 6, 2017.
U.S. Appl. No. 13/453,840 Office Action dated Aug. 21, 2012.
U.S. Appl. No. 13/704,231 Office Action dated Aug. 2, 2016.
U.S. Appl. No. 13/704,231 Office Action dated Feb. 11, 2016.
U.S. Appl. No. 13/704,231 Office Action dated Jan. 19, 2017.
U.S. Appl. No. 13/704,231 Office Action dated Jun. 4, 2015.
U.S. Appl. No. 13/796,761 Office Action dated Dec. 9, 2014.
U.S. Appl. No. 13/802,204 Office Action dated Aug. 7, 2015.
U.S. Appl. No. 13/802,204 Office Action dated Feb. 26, 2015.
U.S. Appl. No. 13/802,204 Office Action dated Jan. 22, 2016.
U.S. Appl. No. 13/802,204 Office Action dated Oct. 4, 2016.
U.S. Appl. No. 13/802,204 Office Action dated Sep. 7, 2017.
U.S. Appl. No. 13/802,264 Office Action dated Jul. 16, 2015.
U.S. Appl. No. 13/802,264 Office Action dated Nov. 28, 2014.
U.S. Appl. No. 13/802,359 Office Action dated Dec. 10, 2014.
U.S. Appl. No. 13/802,447 Office Action dated Dec. 15, 2014.
U.S. Appl. No. 14/125,301 Office Action dated Aug. 19, 2016.
U.S. Appl. No. 14/240,712 Office Action dated Apr. 6, 2017.
U.S. Appl. No. 14/240,712 Office Action dated Nov. 27, 2015.
U.S. Appl. No. 14/240,712 Office Action dated Nov. 28, 2016.
U.S. Appl. No. 14/729,489 Office Action dated Dec. 7, 2016.
U.S. Appl. No. 14/819,319 Office Action dated Apr. 1, 2016.
U.S. Appl. No. 14/819,319 Office Action dated Oct. 2, 2015.
U.S. Appl. No. 14/848,143 Office Action dated Jun. 21, 2017.
U.S. Appl. No. 14/848,143 Office Action dated Oct. 20, 2016.
U.S. Appl. No. 14/848,148 Office Action dated Mar. 20, 2017.
U.S. Appl. No. 14/848,148 Office Action dated Oct. 28, 2016.
U.S. Appl. No. 14/848,153 Office Action dated Apr. 21, 2017.
U.S. Appl. No. 14/848,153 Office Action dated Oct. 25, 2016.
U.S. Appl. No. 14/880,135 Office Action dated Dec. 23, 2016.
U.S. Appl. No. 14/886,946 Office Action dated Apr. 18, 2016.
U.S. Appl. No. 14/886,946 Office Action dated May 19, 2017.
U.S. Appl. No. 14/886,946 Office Action dated Oct. 5, 2016.
U.S. Appl. No. 14/996,051 Office Action dated Jul. 24, 2017.
Verbeek et al. Induction of alpha-smooth muscle actin expression in cultured human brain pericytes by transforming growth factor-beta 1. Am. J. Pathol. 144:372-382 (1994).
Wisniewski et al. Cytokine-induced gene expression at the crossroads of innate immunity, inflammation and fertility: TSG-6 and PTX3/TSG-14. Cytokine Growth Factor Rev 15(2-3):129-146 (2004).
Wu et al. Wound healing effects of porcine placental extracts on rats with thermal injury. Br J Dermatol 148(2):236-245 (2003).
Yamaguchi et al. Negative regulation of transforming growth factor-ß by the proteoglycan decorin. Nature 346(6281):281-284 (1990).
Yoshida. Placenta Power: for Health and Beauty—A useful guide for those seeking placenta-based remedies. Downloaded from http://www.melsmon.co.jp/img/commom/PlacentaPowerp002-121_04-09-08.pdf. (p. 1-41) (Aug. 2001).
Yosuf et al. Challenges in validating the sterilisation dose for processed human amniotic membranes. Radiation Physics and Chemistry 76:1756-1756 (2007).
Sood et al. Gene expression patterns in human placenta. PNAS 103(16):5478-5483 (2006).
U.S. Appl. No. 14/886,946 Office Action dated Oct. 25, 2019.
U.S. Appl. No. 14/996,051 Office Action dated Dec. 5, 2019.

* cited by examiner

COMPOSITIONS OF MORSELIZED UMBILICAL CORD AND/OR AMNIOTIC MEMBRANE AND METHODS OF USE THEREOF

CROSS-REFERENCE TO RELATED APPLICATIONS

This application is a continuation of U.S. application Ser. No. 14/729,489, filed Jun. 3, 2015, now issued as U.S. Pat. No. 9,808,491 on Nov. 7, 2017, which claims priority to U.S. Provisional Application No. 62/109,483, filed on Jan. 29, 2015 and U.S. Provisional Application No. 62/007,167 filed on Jun. 3, 2014, each of which are hereby incorporated by reference in their entireties.

FIELD OF THE INVENTION

The invention relates generally to the fields of biology and health sciences. More particularly, the invention relates to compositions and methods for modulating cellular physiology and pathological processing using a combination of compounds that can be found in morselized amniotic membrane tissue and morselized umbilical cord tissue preparations.

BACKGROUND OF THE INVENTION

The placenta is a temporary organ that surrounds the fetus during gestation. The placenta allows for transport of gases and nutrients, and also provides other metabolic and endocrine functions. The placenta is composed of several tissue types. The umbilical cord (UC) connects the placenta to the fetus, and transports oxygen to the fetus. The umbilical cord has two arteries and a vein. Wharton's jelly, a specialized gelatinous connective tissue material, is within the umbilical cord and protects and insulates the umbilical arteries and vein. The outermost layer of the amniotic sac is known as the "chorion." Much of the placental disc is composed of chorionic villi, which are extensions of the chorionic villous tree. Through these structures, fetal nutrition exchange occurs. The amniotic membrane (AM) is an avascular membranous sac that is filled with amniotic fluid. This membrane is the innermost membrane surrounding a fetus in the amniotic cavity. This tissue consists of an epithelial layer and a subadjacent avascular stromal layer.

The umbilical cord (UC) and amniotic membrane (AM) are rich in stem cells and the resulting morselized umbilical cord and amniotic membrane compositions will therefore meet an unfilled need in the fields of wound care and tissue regeneration.

SUMMARY OF THE INVENTION

Described herein are compositions of morselized amniotic membrane tissue and morselized umbilical cord tissue (that is, compositions that are prepared from amniotic membrane materials, including the amniotic membrane, umbilical cord, amniotic stroma and amniotic jelly, amniotic fluid and Wharton's jelly). In some embodiments, at least one component of the compositions are obtained from amniotic membrane tissue or umbilical cord tissue preparations. Also described herein are compositions in which at least one component of the composition is obtained from human placenta, amniotic fluid and chorion. Also described herein are methods for preparing any of the aforementioned compositions and preparations. Also described herein are methods for storing and preserving any of the aforementioned compositions and preparations. Also described herein are methods for using any of the aforementioned compositions and preparations, including preservative methods, cell culture methods, tissue culture methods, therapeutic methods, prophylactic methods and cosmetic methods. Also described herein are apparatuses comprising compositions of morselized amniotic membrane tissue and morselized umbilical cord tissue on an inert support. Also described herein are methods for preparing the aforementioned apparatuses. Also described herein are methods for using any of the aforementioned apparatuses, including preservative methods, cell culture methods, tissue culture methods, therapeutic methods, prophylactic methods and cosmetic methods.

Various umbilical cord and amniotic membrane compositions exert a number of physiologically significant effects in mammalian cells and intact mammalian tissues. Such effects include suppressing TGF β signaling, increasing apoptosis of macrophages, decreasing cellular proliferation of, decreasing cellular migration of, and increasing apoptosis of vascular endothelial cells, protecting corneal and limbal epithelial cells and keratocytes from apoptosis induced by storage or by dispase treatment, and decreasing inflammation in tissues. Additionally the morselized umbilical cord and amniotic membrane compositions described herein can be in liquid, semi-liquid or lyophilized form.

Although compositions, materials, and methods similar or equivalent to those described herein can be used in the practice or testing of the present invention, suitable preparations, methods and materials are described herein. All publications mentioned herein are incorporated by reference in their entirety. In the case of conflict, the present specification, including definitions will control. In addition, the particular embodiments discussed below are illustrative only and not intended to be limiting.

BRIEF DESCRIPTION OF THE FIGURE

FIG. 1—Depiction of Morselized umbilical cord and amniotic membrane composition on inert support.

DETAILED DESCRIPTION

Certain Definitions

The term "acceptable" with respect to a formulation, composition or ingredient, as used herein, means having no persistent detrimental effect on the general health of the subject being treated.

The term "morsel" as used herein, refers to particles of tissue ranging in size from about 0.1 mm to about 1.0 cm in length, width, or thickness that have been obtained from a larger piece of tissue. A "morsel" as described herein, retains the characteristics of the tissue from which it was obtained and upon inspection is identifiable as said tissue.

The terms "morselized", "morselizing" and "morselization" refer to actions involving the "morsels" of the present application.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein, is an amount effective to achieve a desired effect or therapeutic improvement without undue adverse side effects. It is understood that "an effective amount" or "a therapeutically effective amount" can vary from subject to subject, due to variation in metabolism of the composition, age, weight, general condition of the subject, the condition being treated, the severity of the condition being treated, and the judgment of the prescribing physician.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "kit" and "article of manufacture" are used as synonyms.

By "pharmaceutically acceptable," as used herein, refers to a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutical combination" as used herein, means a product that results from the mixing or combining of more than one active ingredient and includes both fixed and non-fixed combinations of the active ingredients. The term "fixed combination" means that the active ingredients, e.g. the umbilical cord and amniotic membrane compositions described herein and a co-agent, are both administered to a patient simultaneously in the form of a single entity or dosage. The term "non-fixed combination" means that the active ingredients, e.g. the umbilical cord and amniotic membrane compositions described herein and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "protein" as used herein can be the full length polypeptide, or a fragment or segment of a polypeptide, and can encompass a stretch of amino acid residues of at least about 8 amino acids, generally at least 10 amino acids, more generally at least 20 amino acids, often at least 30 amino acids, more often at least 50 amino acids or more of the full length polypeptide.

The term "inert support" as used herein refers to a biocompatible material capable of being applied to a tissue of a patient in need of treatment. Such materials may take the form of sheets. Further, such materials may take the form of mesh sheets. Additionally, such materials may be manufactured from any biocompatible compound such as, for example, collagen; hydrogels; polyethylene glycols; poly(lactic-co-glycolic acids); keratin; hydrophilic polyurethanes; and hydrocolloids As used herein, the term "subject" is used to mean an animal, preferably a mammal, including a human or non-human. The terms patient and subject may be used interchangeably.

The terms "treat," "treating" or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

All publications and patent applications mentioned in this specification are herein incorporated by reference to the same extent as if each individual publication or patent application was specifically and individually indicated to be incorporated by reference.

Compositions

Described herein are compositions that exert a number of physiologically significant effects in mammalian cells. intact mammalian tissues and mammalian patients in need thereof. The compositions comprise at least one of two components: morselized amniotic membrane tissue and morselized umbilical cord tissue.

Any or all of the components of the compositions described herein can be prepared from a human amniotic material, including human amniotic jelly preparations and extracts (as described herein), human amniotic membrane preparations and extracts (as described herein), and human amniotic stroma preparations and extracts (as described herein) or a human umbilical cord material (as described herein) including human Wharton's jelly preparations and extracts (as described herein).

These two components can suppress TGF β promoter activity; increase apoptosis in macrophages; decrease proliferation, decrease migration, and increase apoptosis of human vascular endothelial cells; decrease viability of human fibroblasts; decrease inflammation; and prevent apoptosis of epithelial cells exposed to storage and injury.

These components can be obtained from any suitable source. For example, at least one of the components can be obtained from human tissues, such as amniotic membrane, amniotic jelly, amniotic stroma, amniotic fluid, or a combination thereof. At least one of the components can be obtained from commercial sources. At least one of the components can be isolated from a transgenic organism. The protein sequences can have a similarity of at least 90%, 93%, 95%, 97%, 99% or 99.5% to the human protein sequence. The components can be purified, substantially purified, partially purified, or non-purified. The components can also be prepared from mammalian amniotic membrane tissues, as each of the components is present in amniotic membrane tissues.

Human placental material can be obtained, for example, from sources such as Bio-Tissue, Inc. (Miami, Fla.) and Baptist Hospital (Miami, Fla.) (under IRB approval). The tissue is typically obtained in either a fresh or frozen state. The tissue can be washed to remove excess storage buffer, blood, or contaminants. The excess liquid can be removed, for example, using a brief centrifugation step, or by other means. The tissue can be frozen, using, for example, liquid nitrogen or other cooling means, to facilitate the subsequent homogenization. The source of the umbilical cord and amniotic membrane tissue can be a human. However, other sources of umbilical cord and amniotic membrane tissue, such as bovine or porcine umbilical cord and amniotic membrane tissue, can be used.

A mixture of amniotic membrane tissue and umbilical cord tissue in any ratio from 0.001:99.999 w/w % to 99.999:0.001 w/w % can be morselized from either fresh or frozen tissue through the use of any morselizing tool known to one of skill in the art such as, for example, tissue grinder, sonicator, bread beater, freezer/mill, blender, mortar/pestle, Roto-stator, kitchen chopper, grater, ruler and scalpel to yield morsels ranging in size from about 0.1 mm to about 1.0 cm in length, width, or thickness. Optionally, the resulting morsels may be homogenized to yield consistently sized morsels. The resulting morsels may be either used wet, partially dehydrated or essentially dehydrated by any means known to one of skill in the art such as, for example, centrifuge or lyophilization. The resulting composition may be used immediately or stored for later use in any type of contained known to one of skill in the art such as, for example, pouch, jar, bottle, tube, ampule and pre-filled syringe. Finally, the morsel composition may be sterilized by any method known to one of skill in the art such as, for example, γ radiation.

The placenta can be used to prepare the composition. Umbilical cord and amniotic membrane preparations can include components or portions extracted from intact placentas. If desired, certain components of the umbilical cord and amniotic membrane preparation can be isolated from the preparation at any time during the process. The preparation can be dried, if desired.

The tissue can be frozen prior to the morselizing process. The freezing step can occur by any suitable cooling process. For example, the tissue can be flash-frozen using liquid nitrogen. Alternatively, the material can be placed in an isopropanol/dry ice bath or can be flash-frozen in other coolants. Commercially available quick freezing processes can be used. Additionally, the material can be placed in a freezer and allowed to equilibrate to the storage temperature more slowly, rather than being flash-frozen. The tissue can be stored at any desired temperature. For example, −20° C. or −80° C. or other temperatures can be used for storage.

Morselizing the tissue while frozen, rather than morselizing the tissue prior to freezing, is one optional method for preparing the tissue. Alternatively, fresh, partially thawed, or thawed tissue can be used in the morselizing step. The tissue (fresh, frozen, or thawed) can then be sliced into pieces of a desired size with a suitable device, such as a scalpel, and homogenized with a homogenization device such as a laboratory blender, in a suitable solution. Exemplary solutions include but are not limited to phosphate buffered saline (PBS), DMEM, NaCl solution, and water. The pH of the solution can be adjusted as needed. In some embodiments, the pH range is from about 5.5 or 6.0 to about 8.5. In some embodiments, the frozen tissue is morselized in a solution having a pH of between about 6.3, about 6.6, or about 7.0 to about 7.4, about 7.6, or about 7.8.

Umbilical cord and amniotic membrane preparations can be in a liquid, suspension, or lyophilized forms. Antimicrobial agents such as antibiotics or anti-fungal agents may be added. The material can be packaged and stored, for example, at room temperature, or for example, at −20° C. or −80° C. prior to use.

In some embodiments, the preparation is present as a dry formulation. A dry formulation can be stored in a smaller volume, and may not require the same low temperature storage requirements to keep the formulation from degrading over time. A dry formulation can be stored and reconstituted prior to use. The dry formulation can be prepared, for example, by preparing the freeze-morselized umbilical cord and amniotic membrane tissue as described herein, then removing at least a portion of the water in the composition. The excess water can be removed from the preparation by any suitable means. An exemplary method of removing the water is by use of lyophilization using a commercially available lyophilizer or freeze-dryer. Suitable equipment can be found, for example, through Virtis, Gardiner, N.Y.; FTS Systems, Stone Ridge, N.Y.; and SpeedVac (Savant Instruments Inc., Farmingdale, N.Y.). The amount of water that is removed can be from about 5%, 10%, 20%, 30% to about 60, 70, 80, 90, 95 or 99% or more. In some embodiments, substantially all of the excess water is removed. The lyophilized composition can then be stored. The storage temperature can vary from less than about −196° C. −80° C., −50° C., or −20° C. to more than about 23° C. If desired, the composition can be characterized (weight, protein content, etc.) prior to storage.

The lyophilized composition can be reconstituted in a suitable solution or buffer prior to use. Exemplary solutions include but are not limited to PBS, DMEM, and BSS. The pH of the solution can be adjusted as needed. The concentration of the umbilical cord and amniotic membrane can be varied as needed. In some procedures a more concentrated preparation is useful, whereas in other procedures, a solution with a low concentration of umbilical cord and amniotic membrane is useful. Additional compounds can be added to the composition. Exemplary compounds that can be added to the reconstituted formulation include but are not limited to pH modifiers, buffers, collagen, hyaluronic acid (HA), antibiotics, surfactants, stabilizers, proteins, and the like. The lyophilized umbilical cord and amniotic membrane composition can also be added to a prepared cream, ointment or lotion to result in the desired concentration.

Apparatuses:

Described herein are apparatuses that when contacted with a tissue of a patient in need of treatment exert a number of physiologically significant effects in mammalian cells and intact mammalian tissues. The apparatuses comprise at least one tissue selected from the group consisting of: morselized amniotic membrane tissue; morselized umbilical cord tissue; and combinations thereof; and at least one inert support, wherein, the at least one tissue is dispersed upon at least one surface of the at least one inert support.

In certain embodiments, the at least one tissue comprises pieces of amniotic membrane tissue from about 0.3 mm to about 1.0 cm in length, width and thickness. Further, in certain embodiments, the at least one tissue comprises pieces of umbilical cord tissue from about 0.3 mm to about 1.0 cm in length, width and thickness. Finally, in certain embodiments, the at least one tissue may be present in any ratio from about 0.001:99.999 w/w % to about 99.999:0.001 w/w % of morselized amniotic membrane tissue to morselized umbilical cord tissue, respectively.

In other embodiments, the at least one tissue has a reduced water content by weight percentage. In still other embodiments, the at least one tissue has a water content by weight percentage greater than 20%.

In some embodiments, the apparatus is sterilized. In additional embodiments, the sterilization is accomplished by gamma (γ) radiation. In some embodiments, the at least one inert support is a mesh sheet having an average pore size from about 0.2 mm to about 0.9 cm.

In certain embodiments, the at least one inert support comprises a material selected from the group consisting of: collagen; hydrogels; keratin; hydrophilic polyurethane; polyethylene glycols; poly(lactic-co-glycolic acids); and hydrocolloids. Further, in certain embodiments, the natural biological activity of the morselized amniotic membrane tissue and the morselized umbilical cord tissue is substantially preserved for at least 15 days after initial procurement. Additionally, in certain embodiments, the apparatus is anti-inflammatory, anti-scarring, anti-angiogenic, anti-adhesion, or promotes wound healing when contacted with an exogenous living cell. In some embodiments substantially all red blood cells have been removed from the morselized amniotic membrane tissue and the morselized umbilical cord tissue. In some embodiments, substantially all chorion tissue has been removed from the morselized amniotic membrane tissue and the morselized umbilical cord tissue. In some embodiments, at least some chorion tissue remains with the morselized amniotic membrane tissue and the morselized umbilical cord tissue. In some embodiments, the at least one tissue further comprises amniotic fluid In other embodiments, the at least one tissue is cryopreserved, lyophilized, or a combination thereof. In some embodiments, the at least one inert support has a surface area from about 6 cm$^2$ to about 200 cm$^2$. In some embodiments, the apparatus further comprises at least one additional type of cell selected from the group consisting of: limbal epithelial stem cells, keratocytes, human umbilical vein endothelial cells, mesenchymal stem cells, adipose-derived stem cells, endothelial stem cells and dental pulp stem cells. In some embodiments, the at least one tissue is a morselized homogenate.

The following procedures represent illustrative methods for preparing the umbilical cord and amniotic membrane compositions described and used herein.

Preparation of Preserved Human Umbilical Cord and Amniotic Membrane:

Human placenta was collected at elective cesarean delivery (Heiligenhaus et al., Invest Ophthalmol Vis Sci. 42:1969-1974, 2001, Lee and Tseng, Am J Ophthalmol. 123:303-312, 1997, Prabhasawat et al., Ophthalmology, 104:974-985, 1997, Tseng et al., Arch Ophthalmol. 116:431-441, 1998). The umbilical cord and amniotic membrane was flattened onto nitrocellulose paper (Hybond N+, Amersham, England), with the epithelium surface up. The umbilical cord and amniotic membrane samples were stored at −80° C. in DMEM/glycerol 1:2 (v/v) until use.

Umbilical Cord and Amniotic Membrane Compositions

Umbilical cord and amniotic membrane compositions can be formulated for administration purposes as a non-solid dosage form, for example, by combining with a delivery vehicle to create compositions such as solutions, drops, suspensions, pastes, sprays, ointments, oils, emulsions, aerosols, a coated bandage, a patch, creams, lotions, gels, and the like. The formulation used will depend upon the particular application. Gels are useful for administering the compositions because they allow better retention of the active ingredient at the site of introduction, allowing the active ingredient to exert its effect for a longer period of time before clearance of the active ingredient. A description of exemplary pharmaceutically acceptable carriers or vehicles and diluents, as well as pharmaceutical formulations, is provided herein and can also be found in Remington's Pharmaceutical Sciences, a standard text in this field, and in USP/NF.

Compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. A summary of pharmaceutical compositions described herein may be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins; 1999), herein incorporated by reference in their entirety.

In certain embodiments, the compositions include a pharmaceutically acceptable diluent(s), excipient(s), or carrier(s). In addition, the umbilical cord and amniotic membrane compositions described herein can be administered as compositions in which umbilical cord and amniotic membrane compositions described herein are mixed with other active ingredients, as in combination therapy. In some embodiments, the compositions may include other medicinal or pharmaceutical agents, carriers, adjuvants, such as preserving, stabilizing, wetting or emulsifying agents, solution promoters, salts for regulating the osmotic pressure, and/or buffers. In addition, the compositions can also contain other therapeutically effective substances.

A composition, as used herein, refers to a mixture of a umbilical cord and amniotic membrane compositions described herein with other chemical components, such as carriers, stabilizers, diluents, dispersing agents, suspending agents, thickening agents, and/or excipients. The composition facilitates administration of the compound to an organism. In practicing the methods of treatment or use provided herein, therapeutically effective amounts of umbilical cord and amniotic membrane compositions described herein are administered to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

Topical Formulations

Formulations of the umbilical cord and amniotic membrane compositions described herein include those suitable for topical administration. The formulations may conveniently be presented in unit dosage form and may be prepared by any methods well known in the art of pharmacy. The amount of active ingredients which can be combined with a carrier material to produce a single dosage form will vary depending upon the host being treated and the particular mode of administration.

Suspensions may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Typical compositions described herein include a wide variety of physical forms. These include, but are not limited to, solutions, lotions, creams, oils, gels, sticks, sprays, ointments, balms, shampoo, and pastes. Generally, such carrier systems can be described as being solutions, emulsions, gels, solids, and aerosols. The compositions may be applied topically to the skin, or may be applied in the form of a transdermal delivery device, such as a microneedle, a patch, bandage, or gauze pad known in the art.

The ointments, pastes, creams and gels may contain, in addition to the umbilical cord and amniotic membrane compositions described herein, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the umbilical cord and amniotic membrane compositions described herein, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Solvents are generally employed in the preparation of suitable topical compositions. Such solvents can either be aqueous or organic based. The solvent must be capable of having dispersed or dissolved therein the active ingredients while not being irritating to the animal being treated. Water forms the basis for all aqueous solvents, while suitable organic solvents include propylene glycol, butylene glycol, polyethylene glycol, polypropylene glycol, glycerol, 1,2,4-butanetriol, sorbitol esters, 1,2,6-hexanetriol, ethanol, isopropanol, butanediol, and mixtures thereof. Solvents can be included in the overall composition in amounts ranging from 0.1% to 99% and preferably from 2.0% to 75%. In some embodiments, the compositions are produced in the form of an emollient-containing composition. A wide variety of suitable emollients are known and may be used herein.

In some embodiments, the compositions are formulated as lotions containing from about 0.01% to 10% of the umbilical cord and amniotic membrane compositions described herein. In other embodiments, the compositions are formulated in a solution carrier system as a cream. A cream composition would preferably comprise from about 0.1% to 15% and preferably from 1% to 5% of the umbilical cord and amniotic membrane compositions described herein. Lotions and creams can be formulated as emulsions as well as solutions. The compositions may also be administered in liquid form, including in the form of liposomes suspended in liquid, as in the different type of sprays available in this industry.

In other embodiments, the active ingredients are formulated as ointments. Suitable ointments may comprise simple bases of animal or vegetable oils, or semi-solid hydrocarbons (oleaginous). Suitable ointments may also comprise absorption ointment bases which absorb water to form emulsions. Ointment carriers may also be water soluble. An ointment may comprise from 1% to 99% of an emollient plus to about 0.1% to 99% of a thickening agent.

The proportion of the umbilical cord and amniotic membrane compositions described herein in the compositions can vary from between about 0.01 wt. % to about 100 wt. %, more preferably from about 0.1 wt. % to about 99.9 wt. %, and especially from about 1.0 wt. % to about 99.0 wt. %.

"Carriers" or "vehicles" preferably refer to carrier materials suitable for topical administration and include any such materials known in the art, such as any liquid, gel solvent, liquid diluent, solubilizer, or the like, which is non-toxic, and which does not interact with other components of the composition in a deleterious manner. Examples of suitable carriers for use herein include water, silicone, liquid sugars, waxes, oils, petroleum jelly, and a variety of other materials.

In some embodiments, the carrier or vehicle includes one or more solvents, oils, surfactants, humectants, thickening agents, antioxidants, chelating agents, buffers, and preservatives.

Examples of solvents include C2-C10 alcohols, such as hexanol, cyclohexanol, benzyl alcohol, 1,2-butanediol, glycerol, and amyl alcohol; C5-C10 hydrocarbons such as n-hexane, cyclohexane, and ethylbenzene; C4-C10 aldehydes and ketones, such as heptylaldehyde, cyclohexanone, and benzylaldehyde; C4-C10 esters, such as amyl acetate and benzyl propionate; ethereal oils, such as oil of *eucalyptus*, oil of rue, cumin oil, limonene, thymol, and 1-pinene; halogenated hydrocarbons having 2-8 carbon atoms, such as 1-chlorohexane, 1-bromohexane, and chlorocyclohexane.

Examples of oils comprise fats and oils such as olive oil and hydrogenated oils; waxes such as beeswax and lanolin; hydrocarbons such as liquid paraffin, ceresin, and squalane; fatty acids such as stearic acid and oleic acid; alcohols such as cetyl alcohol, stearyl alcohol, lanolin alcohol, and hexadecanol; and esters such as isopropyl myristate, isopropyl palmitate and butyl stearate.

Examples of surfactants include anionic surfactants such as sodium stearate, sodium cetyl sulfate, polyoxyethylene laurylether phosphate, sodium N-acyl glutamate; cationic surfactants such as stearyldimethylbenzylammonium chloride and stearyltrimethylammonium chloride; ampholytic surfactants such as alkylaminoethylglycine hydrochloride solutions and lecithin; and nonionic surfactants such as glycerin monostearate, sorbitan monostearate, sucrose fatty acid esters, propylene glycol monostearate, polyoxyethylene oleylether, polyethylene glycol monostearate, polyoxyethylene sorbitan monopalmitate, polyoxyethylene coconut fatty acid monoethanolamide, polyoxypropylene glycol (e.g., the materials sold under the trademark "Pluronic"), polyoxyethylene castor oil, and polyoxyethylene lanolin.

Examples of humectants include glycerin, 1,3-butylene glycol, and propylene glycol; examples of thickening agents include xanthan gum, hydroxypropyl cellulose, hydroxypropyl methyl cellulose, polyethylene glycol and sodium carboxymethyl cellulose; examples of antioxidants comprise butylated hydroxytoluene, butylated hydroxyanisole, propyl gallate, citric acid and ethoxyquin; examples of chelating agents include disodium edetate and ethanehydroxy diphosphate; examples of buffers comprise citric acid, sodium citrate, boric acid, borax, and disodium hydrogen phosphate; and examples of preservatives are methyl parahydroxybenzoate, ethyl parahydroxybenzoate, dehydroacetic acid, salicylic acid and benzoic acid.

In certain embodiments, the carrier/vehicle is composed of the foregoing materials to achieve a controlled occlusion of the skin, thereby resulting in optimal enhancement of biologically active moiety penetration across the skin with minimal skin irritation. In certain embodiments, the carrier/vehicle may include a dispersing agent that aids in maintaining a particulate phase of the active ingredients dispersed in the continuous phase. In other embodiments, non-ionic excipients, such as lauric alcohol, propylene glycol monolaurate, myristyl lactate, lauryl lactate, or the like, facilitate dispersion.

The rate of biologically active moiety delivery across a dermal surface can be increased by transdermal delivery enhancers. Suitable transdermal delivery enhancers include proton-accepting solvents such as dimethylsulfoxide and dimethylacetamide. Other suitable transdermal delivery enhancers include 2-pyrrolidine, N,N-diethyl-m-toluamide, 1-dodecylazacycloheptan-2-one, N,N-dimethylformamide, N-methyl-2-pyrrolidine, terpenes, surfactants, and calcium thioglycolate.

Suitable dermal penetration enhancers include 1-5 carbon fatty acid esters of para-aminobenzoic acid, isopropyl palmitate, isopropyl myristate, ethanol, isobutyl alcohol, isobutyl alcohol, stearyl alcohol, glycerol, 2-pyrrolidone, urea, propylene glycol, oleic acid, palmitic acid, dimethyl sulfoxide, N,N-dimethyl acetamide, N,N-dimethyl formamide, 2-pyrrolidone, 1-methyl-2-pyrrolidone, 5-methyl-2-pyrrolidone, 1,5-dimethyl-2-pyrrolidone, 1-ethyl-2-pyrrolidone, 2-pyrrolidone-5-carboxylic acid, N,N-dimethyl-m-toluamide, urea, ethyl acetate, 1-dodecylazacycloheptan-2-one, oleic acid, imidazoline, butylurea, and pyrrolidone carboxylic acid esters.

Wetting agents, emulsifiers, surfactants, and lubricants, such as sodium lauryl sulfate and magnesium stearate, as well as coloring agents, release agents, coating agents, sweetening, flavoring, and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

As appropriate compositions for topical application there may be cited all compositions usually employed for topically administering therapeutics, e.g., creams, jellies, dressings, shampoos, tinctures, pastes, ointments, salves, powders, liquid or semiliquid formulations, and the like. Application of said compositions may be by aerosol, e.g., with a propellant such as nitrogen carbon dioxide, a freon, or without a propellant such as a pump spray, drops, lotions, or a semisolid such as a thickened composition which can be applied by a swab. In particular compositions, semisolid compositions such as salves, creams, pastes, jellies, ointments, and the like will conveniently be used.

Methods of Dosing and Treatment Regimens

The compositions can be administered by any suitable technique. Typically, the compositions will be administered directly to a target site (e.g., wound. dermal ulcer, skin).]. If delivery of umbilical cord and amniotic membrane preparations to the skin is desired, topical administration can be used.

The compositions containing the umbilical cord and amniotic membrane compositions described herein can be administered for [therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician. It is considered well within the skill of the art for one to determine such therapeutically effective amounts by routine experimentation (including, but not limited to, a dose escalation clinical trial).

Combination Treatments

The umbilical cord and amniotic membrane compositions and methods described herein may also be used in conjunction with other well-known therapeutic reagents that are selected for their particular usefulness against the condition that is being treated. In general, the compositions described herein and, in embodiments where combinational therapy is employed, other agents do not have to be administered in the same composition, and may, because of different physical and chemical characteristics, have to be administered by different routes. The determination of the mode of administration and the advisability of administration, where possible, in the same composition, is well within the knowledge of the skilled clinician. The initial administration can be made according to established protocols known in the art, and then, based upon the observed effects, the dosage, modes of administration and times of administration can be modified by the skilled clinician.

The particular choice of compounds used will depend upon the diagnosis of the attending physicians and their judgment of the condition of the patient and the appropriate treatment protocol. The compounds may be administered concurrently (e.g., simultaneously, essentially simultaneously or within the same treatment protocol) or sequentially, depending upon the nature of the disease, disorder, or condition, the condition of the patient, and the actual choice of compounds used. The determination of the order of administration, and the number of repetitions of administration of each therapeutic agent during a treatment protocol, is well within the knowledge of the skilled physician after evaluation of the disease being treated and the condition of the patient.

It is known to those of skill in the art that therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature. Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations are also envisioned.

It is understood that the dosage regimen to treat or ameliorate the condition(s) for which relief is sought, can be modified in accordance with a variety of factors. These factors include the disorder from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

In addition, the umbilical cord and amniotic membrane compositions described herein also may be used in combination with procedures that may provide additional or synergistic benefit to the patient. By way of example only, patients are expected to find therapeutic and/or prophylactic benefit in the methods described herein, wherein composition of a compound disclosed herein and/or combinations with other therapeutics are combined with genetic testing to determine whether that individual is a carrier of a mutant gene that is known to be correlated with certain diseases or conditions.

Kits/Articles of Manufacture

For use in the therapeutic applications described herein, kits and articles of manufacture are also described herein. Such kits can include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, bottles, and any packaging material suitable for a selected formulation and intended mode of administration and treatment. A wide array of formulations of the compounds and compositions provided herein are contemplated as are a variety of treatments for any disease, disorder, or condition.

For example, the container(s) can include one or more umbilical cord and amniotic membrane compositions described herein, optionally in a composition or in combination with another agent as disclosed herein. The container (s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically include one or more additional containers, each with one or more of various materials (such as reagents, optionally in concentrated form, and/or devices) desirable from a commercial and user standpoint for use of the umbilical cord and amniotic membrane compositions described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, the compositions or apparatuses can be presented in a pack or dispenser device which can contain one or more unit dosage forms containing a compound provided herein. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible carrier can also be prepared, placed in an appropriate container, and labeled for treatment of an indicated condition.

Methods of Treatment

The umbilical cord and amniotic membrane compositions and apparatuses described herein have many uses including research and clinical applications. Based on the results described herein, the umbilical cord and amniotic membrane compositions described herein can be applied to tissues, cells or patients in need thereof to achieve a desired modulation of physiology.

Specifically, the umbilical cord and amniotic membrane compositions and apparatuses described herein may be useful for treating a patient suffering from a disease or disorder selected from the group consisting of: skin wounds and repairs (e.g. burns, necrosis, skin ulcers and venous ulcers), ocular wounds and repairs (e.g. glaucoma, ocular ulcers, corneal ulcers, conjunctival, scleral and lid and orbital rim reconstruction), cell transplant, coronary wounds and repairs (e.g. coronary artery bypass, heart valve repair/replacement, vein repair and artery repair), nerve repair, spinal repair, psoriasis, plaque psoriasis and rheumatoid arthritis.

Additionally, the umbilical cord and amniotic membrane compositions and apparatuses described may be used as a dermal filler for a patient in need thereof.

Examples

A umbilical cord and amniotic membrane composition as described herein, was slowly poured over 300 μm mesh inert support with the aid of a vacuum filter system. Particles in the desired size range remained upon the inert support to form an apparatus of the present application which may then be used to treat a patient in need thereof.

While it is apparent that the embodiments of the invention herein disclosed are well suited to fulfill the objectives stated above, it will be appreciated that numerous modifications and other embodiments may be implemented by those skilled in the art, and it is intended that the appended claims cover all such modifications and embodiments that fall within the true spirit and scope of the present invention.

A number of references have been cited and the entire disclosures of which are incorporated herein by reference.

What is claimed is:

1. A gel composition, comprising:
   a) a therapeutically effective amount of i) morselized placental amniotic membrane and ii) morselized umbilical cord; and
   b) a pharmaceutically-acceptable excipient;
   wherein water has not been substantially removed from the morselized amniotic membrane or from the morselized umbilical cord; and
   wherein the morselized placental amniotic membrane and the morselized umbilical cord have a particle size from about 0.3 mm to about 1 cm in length, width, and thickness.

2. The gel composition according to claim 1, wherein the gel composition has reduced water content by weight percentage compared to the morselized placental amniotic membrane or the morselized umbilical cord before morselization.

3. The gel composition according to claim 1, wherein the gel composition has a water content greater than 20% by weight percentage.

4. The gel composition according to claim 1, wherein the gel composition is sterilized.

5. The gel composition according to claim 4, wherein the gel composition is sterilized by gamma (γ) radiation.

6. The gel composition according claim 1, wherein the morselized placental amniotic membrane and the morselized umbilical cord have a biological activity that is substantially preserved for at least 15 days after initial procurement of the morselized placental amniotic membrane and the morselized umbilical cord.

7. The gel composition according to claim 1, wherein the composition is anti-inflammatory, anti-scarring, anti-angiogenic, anti-adhesion, promotes wound healing, or a combination thereof.

8. The gel composition according to claim 1, wherein the morselized placental amniotic membrane and the morselized umbilical cord are substantially free of red blood cells.

9. The gel composition according to claim 1, wherein the morselized placental amniotic membrane substantially free of chorion.

10. The gel composition according to claim 1, wherein the morselized placental amniotic membrane further comprises chorion.

11. The gel composition according to claim 1, wherein the gel composition further comprises amniotic fluid.

12. The gel composition according to claim 1, further comprising at least one pharmaceutically acceptable carrier or diluent selected from the group consisting of: acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars, sodium stearoyl lactylate, carrageenan, monoglyceride, diglyceride, pregelatinized starch, lactose, starch, mannitol, sorbitol, dextrose, microcrystalline cellulose, dibasic calcium phosphate, dicalcium phosphate dihydrate; tricalcium phosphate, calcium phosphate; anhydrous lactose, spray-dried lactose, compressible sugar, hydroxypropylmethylcellulose, hydroxypropylmethylcellulose acetate stearate, sucrose, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; sodium chloride, inositol, and bentonite.

13. The gel composition according to claim 1, wherein the morselized placental amniotic membrane, morselized umbilical cord or combination thereof is a homogenate.

14. The gel composition according to claim 1, wherein the morselized placental amniotic membrane and the morselized umbilical cord are homogenized.

15. A method of repairing damaged nerve tissue in an individual in need thereof comprising administering to damaged nerve tissue a therapeutically effective amount of the gel composition according to claim 1.

16. An apparatus comprising: (a) an inert support, and (b) a gel composition of claim 1 disposed on the inert support.

17. The apparatus of claim 16, wherein the inert support is a mesh sheet with an average pore size of about 0.2 mm to about 0.9 cm.

18. The apparatus of claim 16, wherein the inert support comprises a material selected from the group consisting of: collagen; hydrogels; keratin; hydrophilic polyurethane; polyethylene glycols; poly(lactic-co-glycolic acids); and hydrocolloids.

* * * * *